United States Patent [19]

Kiefer et al.

[11] Patent Number: 5,998,680
[45] Date of Patent: Dec. 7, 1999

[54] ISOMERIZATION OF ALLYL ALCOHOLS

[75] Inventors: Matthias Kiefer, Nussloch; Wolfgang Siegel, Limburgerhof; Jörg Therre, Worms; Melanie Pahl; Werner Aquila, both of Mannheim; Ulrich Schäfer-Lüderssen, Ludwigshafen; Udo Rheude, Otterstadt, all of Germany

[73] Assignee: BASF Aktiengesellschaft, Ludwigshafen, Germany

[21] Appl. No.: 09/028,643

[22] Filed: Feb. 24, 1998

[30] Foreign Application Priority Data

Feb. 25, 1997 [DE] Germany ............................ 197 07 385
Sep. 1, 1997 [DE] Germany ............................ 197 38 083

[51] Int. Cl.$^6$ .................................................. C07C 29/56
[52] U.S. Cl. ......................... 568/906; 508/813; 508/875
[58] Field of Search ...................... 508/906, 875, 508/813

[56] References Cited

U.S. PATENT DOCUMENTS 3,696,155  10/1972  Mueller et al. .

FOREIGN PATENT DOCUMENTS 19 25 197  11/1970  Germany .
25 16 698  10/1975  Germany .
54-61110   5/1979   Japan .
181 090    6/1966   U.S.S.R. .

OTHER PUBLICATIONS

Database WPI, Derwent Publications, AN 79–47786B, JP 54 061110, May 17, 1979.

Otto Bayer, et al., "Allgemeines Vorwort", Methoden Der Organischen Chemie, vol. No. VI, 1b, (1984) pp. 528–535.

A.I. Lebedeva, et al., "Research on the Isomerization and Polymerization of Dimethylvinylcarbinol as Functions of the Reagent pH", Journal of General Chemistry, USSR, vol. No. 21, (1951), pp. 1235–1241.

I.N. Nasarow, et al., "Azetylenderivate–Reversible Isomerisation Substituierter Allylalkohole", Bulletin De L'Acadéemië Des Sciences De L'urss, Chemistry Series, (1946), pp. 419–426 (With German Translation).

M. Bertand, et al., "Sur Des Conditions Particulierment Simples de Couplage Isoprenique", Bull.Soc. Chim. Fr. vol. No. 128 (1991), pp. 904–910.

*Primary Examiner*—James H. Reamer
*Attorney, Agent, or Firm*—Oblon, Spivak, McClelland, Maier & Neustadt, P.C.

[57] ABSTRACT

Allyl alcohols are isomerized in aqueous solution in the presence of protonic acids, with the pH of the reaction mixture being adjusted to the range from 2 to 5 with an acid concentration below 0.16 mol per liter of the reaction mixture or with a buffer which comprises the protonic acid.

9 Claims, No Drawings

ISOMERIZATION OF ALLYL ALCOHOLS

The present invention relates to a process for isomerizing precursor allyl alcohols to product allyl alcohols in aqueous solution in the presence of protonic acids.

Allyl alcohols are important intermediates in industrial organic chemistry. Tertiary allyl alcohols in particular are used, for example, as intermediates in the preparation of fragrances or else as additives in soaps or detergents.

It is known that allyl alcohols isomerize with acid catalysis. This isomerization corresponds to a 1,3 migration of the hydroxyl group and a corresponding shift of the double bond, as depicted in the following equation with the formulae I and II:

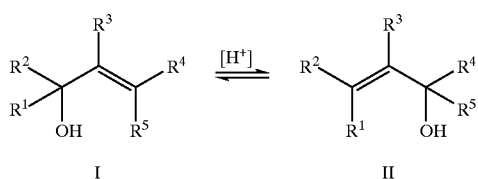

This migration of a double bond and of a substituent is known for allyl compounds and is generally referred to as an allylic rearrangement. Allylic rearrangements of allyl alcohols are equilibrium reactions.

A general review of the isomerization of allyl alcohols catalyzed by protonic acids is given, for example, in Houben-Weyl, Methoden der organischen Chemie, Volume VI, 1b, page 528 et seq., Stuttgart 1984. This describes, inter alia, that such isomerizations can be carried out particularly straightforwardly when a tertiary allyl alcohol with a terminal C=C double bond is transformed into the corresponding primary alcohol with internal C=C double bond.

Accordingly there has been industrial use in the past in particular of the isomerization of dimethylvinylcarbinol (DMVC, 2-methyl-3-buten-2-ol), a tertiary allyl alcohol, to its isomer prenol (3-methyl-2-butenol), a primary allyl alcohol. Dialkyl(alkenyl)carbinols such as DMVC were readily obtainable on the basis of the carbide/acetylene chemistry formerly widely used in industry, by a base-induced condensation of 1-alkynes such as acetylene with ketones such as acetone and subsequent hydrogenation of the triple bond to a double bond. Nowadays, acetylene is a comparatively uncommon and costly raw material. On the other hand, olefins such as dialkylalkenes, for example isobutene, are readily available on the basis of the petrochemical raw materials now customary, and can easily be processed, by condensation with aldehydes such as formaldehyde, and subsequent isomerization of the double bond, to prenol or prenol derivatives such as prenols substituted by organic radicals. The present need in industry is therefore in particular a process with which tertiary allyl alcohols such as DMVC can be prepared from primary allyl alcohols such as prenol.

SU-A 181 090 describes a process for isomerizing prenol to DMVC in which mineral acid, especially sulfuric acid, is employed as catalyst in a concentration below 1% by weight (equivalent to a pH above 0.7), preferably 0.3 to 0.5% by weight. This preferred concentration range corresponds to a pH range from 1.0 to 1.2. This publication also discloses, however, that large amounts of byproducts result in the disclosed process and have to be removed regularly from the reactor.

A. I. Lebedeva and L. L. Shchukovskaya, J. Gen. Chem. USSR, 21 (1951), 1235–1241 investigated the dependence of the isomerization of DMVC on the pH of the reaction medium and on the reaction temperature with reaction times of 30 hours. They found that there was detectable isomerization of the DMVC at room temperature only at a pH of 1.29 or below. At a pH of 1.32 or above there was no isomerization of the DMVC at all, either at room temperature or in a boiling waterbath.

I. N. Nazarov, I. N. Azerbaev and V. N. Rakcheeva disclose in Bull. Acad. Sci. USSR, Chem. Ser. 1946, 419–426, that the isomerization of dialkylvinylcarbinols, ie. tertiary allyl alcohols, to the corresponding primary allyl alcohols takes place "quite smoothly" at a temperature in the range from 60 to 100° C. under the influence of 0.1% strength sulfuric acid, ie. at a pH of about 1.7, while the isomerization at room temperature is carried out under the influence of 1–5% strength sulfuric acid, ie. a pH of about 0.7 or below. This publication discloses further that the isomerization process takes place too slowly at a sulfuric acid concentration of 0.01%, ie. a pH of 2.7, even at 100° C.

The known examples of the isomerization of allyl alcohols have therefore all been carried out with high acid concentrations, ie. at a low pH not exceeding 1.5 or even distinctly below 1, because the opinion prevailing among experts was that otherwise the reaction rate would be too low for economically satisfactory application of the process.

Large amounts of byproducts regularly result at these pH values. This is because allyl alcohols themselves are sensitive to acids, and byproducts are formed on use of strong acids, for example intramolecular elimination of water results in the corresponding dienes, or intermolecular elimination of water or addition reactions result in the corresponding ethers. In addition, if the molecules contain other C=C double bonds, skeletal rearrangements are possible. M. Bertrand, B. Waegell and J. P. Zahra, Bull. Soc. Chim. Fr. 128 (1991) 904–910 describe, for example, the conversion of DMVC in a boiling aqueous solution of 10% by weight oxalic acid into isoprene (2-methyl-1,3-butadiene) and a mixture of various alcohols of the terpene series. A. I. Lebedeva and L. L. Shchukovskaya, loc. cit., found that the prenol formed as isomer of DMVC reacts further to terpenes and sesquiterpenes increasingly at pH values of 1.27 and below.

Other processes attempt to avoid the formation of byproducts. JP-A-54061110 discloses a process for isomerizing allyl alcohols with large amounts of boric acid as catalyst. 0.1 to 60% by weight boric acid, in particular 1 to 30% by weight, are used. Conversions above 90% are achieved only with boric acid concentrations above 7% by weight boric acid, but the selectivity of the isomerization declines rapidly with larger amounts of boric acid.

It is also possible to isomerize allyl alcohols by catalysis with transition metal compounds, for example by the processes disclosed in DE-A-25 16 698 using the tungsten compounds also disclosed therein. The disadvantages in this case are the elaborate synthesis of the tungsten catalysts and the comparatively low conversion, despite the application of temperatures above 150° C. which is necessary.

Thus there remains a great need for a process which allows allyl alcohols to be isomerized in a simple, low-cost and maximally selective manner with, moreover, high space-time yields without the need to employ large amounts of catalyst. In particular, this process ought to allow tertiary allyl alcohols to be prepared from primary or secondary allyl alcohols.

It is an object of the present invention to find a process of this type.

We have found that this object is achieved by a process for isomerizing precursor allyl alcohols to product allyl alcohols in aqueous solution in the presence of protonic acids, wherein the pH of the reaction mixture is adjusted to a range from 2 to 5 either with a protonic acid in a concentration below 0.16 mol per liter of the reaction mixture or with a buffer which comprises the protonic acid.

The process surprisingly shows that the low pH values which were previously used for isomerizing allyl alcohols with mineral acids or buffers as catalysts and which lead to side reactions reducing the yield are unnecessary, and that even primary allyl alcohols can be isomerized satisfactorily at these pH values to give tertiary allyl alcohols. Application of the process according to the invention leads to economically satisfactory space-time yields and economically satisfactory selectivity.

The process further shows, surprisingly, that when buffers are used to adjust the pH it is possible, even with high and/or varying amounts of acidic or basic impurities in the precursor allyl alcohol, to avoid industrially elaborate and/or economically unsatisfactory purification measures, or the necessity therefor can at least be greatly diminished.

The precursor allyl alcohols which can be employed in the process according to the invention have the formula I. The radicals $R^1$, $R^2$, $R^3$, $R^4$ and $R^5$ are, independently of one another, hydrogen or an aliphatic, cycloaliphatic, aromatic, araliphatic or heteroaromatic radical, for example alkyl, alkenyl, alkynyl, cycloalkyl, cycloalkenyl, aryl such as phenyl, alkaravl or aralkyl. The radicals may be substituted by other organic radicals and may comprise heteroatoms, for example in the form of alkoxy substituents, ester groups, amino or alkylamino functionalities. The heteroatoms such as oxygen, sulfur and nitrogen may also form part of an aromatic or cyclic radical. The radicals may also be linked together and form parts of single or polycyclic ring systems with one or more members, for example with 4 to 16 carbon atoms, which comprise the incorporated radicals and one, two or three carbon atoms with the allyl unit.

Examples of precursor allyl alcohols which can be used in the process according to the invention are those where the radicals $R^1$, $R^2$, $R^3$, $R^4$ and $R^5$ are, each independently of one another, hydrogen or linear saturated alkyl radicals having one to 18 carbon atoms, such as methyl, ethyl, propyl, butyl, pentyl, hexyl, heptyl, octyl, nonyl or decyl. The radicals may likewise be saturated cyclic alkyl radicals having three to 12 carbon atoms, such as cyclopentyl, cyclohexyl or cycloheptyl, or else branched saturated alkyl radicals such as 2-propyl, 2-butyl, 2-methyl-1-propyl, 1,1-dimethylethyl or all branched isomeric pentyl, hexyl, heptyl, octyl, nonyl or decyl radicals. They may also be unsaturated radicals having one or more double and/or triple bonds, which are derived from the abovementioned saturated radicals by formal removal of at least two hydrogen atoms located on adjacent carbon atoms, for example vinyl, propenyl, butenyl, 2-propenyl, 2-butenyl or 3-butenyl. They may likewise be aromatic radicals, for example phenyl or 1- or 2-naphthyl. Said radicals may in each case carry substituents which are inert under the reaction conditions, for example halogen, alkyl or alkoxy substituents.

It is preferred to use in the process according to the invention primary allyl alcohols of the formula I where $R^1$ and $R^2$ are hydrogen, or secondary allyl alcohols with the formula I where either $R^1$ or $R^2$ is hydrogen and the other radical is not hydrogen, with $R^4$ and $R^5$ both not being hydrogen both in the primary and in the secondary allyl alcohols, as precursor allyl alcohols. In this case, tertiary allyl alcohols are prepared from primary or secondary allyl alcohols.

A particularly preferred application for the process according to the invention is to synthesize DMVC from prenol. Another preferred application is to synthesize linalool from geraniol or nerol.

A suitable catalyst in the process according to the invention is in principle any monobasic or polybasic inorganic or organic protonic acid able to acidify the reaction mixture into the pH range according to the invention in the amount according to the invention and having anions which are inert toward the employed and produced allyl alcohols. It is also possible in place of pure acids to use mixtures of acids.

Examples of protonic acids which can be employed singly or in a mixture are hydrofluoric acid, hydrochloric acid, perchloric acid, hydrobromic acid, sulfuric acid, sulfonic acids, bisulfates such as potassium or sodium bisulfate, nitric acid, phosphoric acid, dihydrogen phosphates such as potassium and sodium dihydrogen phosphate. Further examples of acids which can be used are organic acids derived from alkanes or aromatic compounds, such as formic acid, acetic acid, propionic acid, butyric acid, 2-ethylhexanoic acid, benzoic acid, oxalic acid, tartaric acid, succinic acid, maleic acid, fumaric acid, adipic acid and citric acid.

The concentration of acid used is generally below 0.16 mol per liter of the reaction mixture, preferably below 0.12 mol per liter and particularly preferably below 0.1 mol per liter. Very much lower concentrations of strong acids, for example sulfuric acid, are needed to adjust the pH range according to the invention. A sulfuric acid concentration generally of about 0.01 mol per liter or less will be sufficient. Weaker acids, for example dihydrogen phosphates, must be used in higher concentrations up to 0.16 mol per liter in order to adjust the pH range according to the invention.

The buffers which can be employed as catalysts in the process according to the invention are those mixtures of acid and salts of their conjugate bases or bases and salts of their conjugate acids which comprise a protonic acid or functionalities with protonic acidity and with which a pH in the pH range used according to the invention can be adjusted. It is generally necessary for the action as buffer that at least part of the conjugate acid-base pair is not a strong acid or base. The term "strong" is normally used to characterize those acids which are virtually completely dissociated, it also being possible in the case of a polybasic acid for only one acid function to be strong; the term "strong" normally also applies conversely to corresponding bases. These buffers can be added as mixture to the reaction mixture, but it is just as possible for the individual constituents of the buffer to be added separately or to be generated in situ, for example by adding a strong acid to the salt of a weak acid or by adding a strong base to the salt of a weak base. It is just as possible to use buffers which do not represent a mixture but combine acidic and basic functions, for example salts of polybasic acids which still contain acidic functions, or polymers which contain both acidic and basic functions. A detailed definition of the term "buffer", which is otherwise generally well known, and a description of the mode of action of buffers is to be found in Römpp's Chemie Lexikon, Volume 5, page 3677, 9th Edition, Stuttgart 1992.

A buffer suitable as catalyst for the isomerization in the process according to the invention is in principle any buffer which comprises a protonic acid and with which a pH in the range from 2 to 5 can be adjusted in the reaction medium. Buffers of this type are known to the skilled worker and are also commercially available.

The buffers preferably used, or their constituents, are preferably inert, apart from catalyzing the isomerization, toward the employed or produced allyl alcohols. The inertness can be checked where appropriate by routine tests.

Examples of buffers which can be employed according to the invention are mixtures of phosphoric acid and sodium phosphate ("phosphate buffer"), lactic acid and sodium lactate ("lactate buffer"), citric acid and sodium citrate ("citrate buffer") or sodium acetate/acetic acid ("acetate buffer") with a pH in the range from 2 to 5.

It is just as possible to use salts of polybasic acids in which acidic functions are still present. Examples thereof are alkali metal salts of polybasic carboxylic acids, such as monosodium oxalate, monosodium tartrate, monosodium succinate, monosodium adipate, monosodium citrate, disodium citrate, monosodium phthalate or the corresponding potassium compounds, or salts of inorganic polybasic acids such as disodium hydrogen phosphate. In these cases it is possible to adjust the pH of the reaction medium exactly to the required value in the range from 2 to 5 by further addition of a strong acid, for example a mineral acid such as sulfuric acid or hydrochloric acid, or a strong base, for example sodium or potassium hydroxide solution. Examples of such buffers are disodium citrate/hydrochloric acid, potassium hydrogen phthalate/hydrochloric acid or disodium hydrogen phosphate/hydrochloric acid.

The use of a citrate buffer is particularly preferred.

The amount of buffer used is not generally critical. Very high buffer concentrations in the reaction medium are usually economically disadvantageous, but have no technical disadvantage as long as the physical properties of the reaction solution (for example viscosity, absence or presence of undissolved solids or a second liquid phase), are essentially unimpaired. However, in general, a buffer content in the reaction medium not exceeding 30% by weight will be sufficient, and the maximum amount of buffer used is preferably 20% by weight and particularly preferably 10% by weight.

The optimal pH to be adjusted in the process according to the invention is generally above 2, in particular above 2.1. The pH is adjusted preferably to at least 2.2 and particularly preferably to at least 2.5. The maximum pH is generally 5, preferably 4.0 and particularly preferably 3.5.

The choice of the pH has an effect on the rate and selectivity of the reaction. A low pH of, for example, 2.0 means a high reaction rate but also a lower selectivity, especially with long product residence times in the reactor. However, this procedure may also be advantageous in some cases, especially if the reaction mixture can be worked up rapidly and the product is thus quickly separated from the acid which is present. If the pH is too high, the selectivity for the product is high but the space-time yields are low. It will be necessary to consider in the specific case which pH and, in particular, which combination of pH, temperature and residence time in the reactor provides the optimum space-time yield and selectivity.

The process according to the invention can be carried out batchwise or continuously.

The process can be carried out, for example, by introducing the acid or the buffer and the solvent into a reaction vessel and adding the allyl alcohol to be isomerized. However, it is equally possible to mix the allyl alcohol and the solvent and to add the acid or the buffer, or to add the allyl alcohol and the acid or buffer simultaneously to the solvent. It is equally possible to add mixtures of solvent and allyl alcohol or of solvent and acid or buffer. It may in the specific case, for example because of the heat produced in the reaction and requiring dissipation, be advantageous to add the allyl alcohol and/or the acid or the buffer or mixtures thereof with solvent not all at once but by metering in several batches or continuously. After the reaction is complete, the mixture of products is worked up.

It may, depending on the chosen type of workup, be advantageous to neutralize the reaction medium after the reaction is complete in order to prevent acid-induced further reactions which reduce the selectivity. It is generally sufficient for this purpose to raise the pH of the reaction medium above 5. This can take place by adding alkaline compounds to the reaction medium. Examples of suitable alkaline compounds are basic compounds such as ammonia, sodium carbonate, sodium phosphate, sodium hydroxide, the corresponding potassium compounds, or aqueous solutions of these compounds.

For workup, in general the product mixture is separated from the reaction solvent. This can take place, for example, by distillation or extraction. Suitable extractants are in principle all those in which the product mixture is more soluble than in water and which are inert toward the required product, the allyl alcohol. The extractants preferably used are those from which the required product can easily be separated, for example by distillation or crystallization. Extractants particularly suitable for the process according to the invention are organic solvents, for example open-chain, branched or cyclic dialkyl ethers such as diethyl ether, dibutyl ether, tert-butyl methyl ether, tert-butyl ethyl ether, tetrahydrofuran or dioxane, aliphatic, alicyclic or aromatic hydrocarbons such as pentane, hexane, cyclopentane, cyclohexane, benzene, toluene or the xylenes, ketones such as acetone, alcohols such as butanol, or other solvents such as acetonitrile, dimethyl sulfoxide, dimethylformamide, N-methylpyrrolidone or sulfolane. The solvent removed from the product mixture can be returned to the reaction.

Following the extraction, the product mixture is separated from the extractant by known processes, for example by distillation or crystallization.

Although the product mixture after removal of the solvent may, when the conversions and selectivities are very high, be virtually pure product allyl alcohol, in general there will be small amounts of byproducts and/or unreacted precursor allyl alcohol present. For this reason, in general, isolation of the product mixture from the reaction medium will be followed by a purification stage, ie. removal of the required product. This removal and purification of the required product can take place by known processes, for example by fractional distillation or fractional crystallization.

It may also be economically worthwhile in certain cases for the unreacted precursor allyl alcohol present in sufficient quantity in the product mixture to be isolated, in the same step as the required product or in a special separation and purification step, in adequate purity and returned to the reaction.

The isomerization is an equilibrium reaction. The position of the equilibrium, ie. the concentrations of precursor allyl alcohol and product allyl alcohol which are set up, depends on their thermal dynamic properties and on the reaction conditions. Removal of the reaction product, discontinuously or, preferably, continuously, from the reaction medium makes it possible to use the isomerization for preparing the required product with satisfactory space-time yields even in cases where the position of the equilibrium results in only unsatisfactory formation of the required product.

The process according to the invention can be carried out continuously, for example, by continuously removing from the reactor a stream of material which is subjected to the steps described above for removing the solvent and fractionating the product mixture. In this way, the required product and any byproducts are removed continuously from the reactor. Unreacted precursor allyl alcohol is introduced together with fresh precursor allyl alcohol and solvent continuously into the reaction. The pH in the reaction vessel can, for example, be continuously monitored by a pH meter and corrected if there are deviations from the required value in the range according to the invention. This correction can take place, for example, by adding buffer or constituents of the buffer mixture, the requirement in the latter case being to add a basic buffer constituent if the pH falls and an acidic buffer constituent if the pH rises.

To avoid accumulation of unwanted components in the reaction medium, it may be advantageous to remove part of the reaction medium discontinuously or continuously from the reactor and replace it by reaction medium which is fresh or recycled after removal of interfering components. This can take place, for example, by disposal or purifying and reprocessing at least part of the stream of material which remains after removal of the product mixture by distillation or extraction.

A particularly simple embodiment emerges when the required product is the component of the reaction mixture with distinctly the lowest boiling point. In this case, the process can be carried out simply as a continuous distillation, with the reaction taking place in the bottom of the distillation column.

The isomerization is generally carried out in aqueous solution. It may be expedient, for example on use of allyl alcohols of low solubility in water, to use mixtures of water with an organic solvent which is miscible with water in the mixing ratio used. Examples of solvents which can be used are acetonitrile, dimethyl sulfoxide, dimethylformamide, tetrahydrofuran, N-methyl-pyrrolidone, ethylene carbonate, propylene carbonate or sulfolane.

The concentration of the allyl alcohol in the solvent is a parameter to be optimized in the individual case. If the concentrations are too high, there is observed to be increased formation of byproducts, for example condensation to ethers, especially in the case of a two-phase mixture. If the concentrations are too low, the workup results in an unnecessarily large dilute stream of material which involves greater expense, for example for intermediate storage, a greater energy consumption, for example for pumping, and greater complexity in the workup, for example because of the need for extraction from a more dilute medium. The optimal range appears to be at and below the maximum solubility of the allyl alcohol in the solvent used. The concentrations used will in the final analysis be determined by considerations of economy, which will generally be satisfactory with an upper limit of 30% by weight of the starting material in the reaction mixture.

The reaction can in general be carried out at ambient temperature. However, to achieve satisfactory space-time yields, it is generally expedient to use a temperature above 50° C. The temperature preferably chosen should be above 60° C. The temperature will generally be chosen to be below the boiling point of the reaction mixture, as a rule below 200° C., preferably below 100° C.

The pressure is not a critical parameter in the process according to the invention but can, for example, be chosen so that the solvent boils at the reaction temperature used. However, atmospheric pressure is preferably used.

The process according to the invention avoids the various disadvantages of the individual known processes and thus makes it possible to isomerize allyl alcohols economically with high yield and selectivity.

EXAMPLES

Comparative Example V1

Examples 1 to 7

Effect of the pH

The amount of acid necessary to adjust to the required pH was dissolved in 500 ml of water. This mixture was introduced with stirring into a reaction vessel and heated to 80° C. After the temperature became constant, the pH was checked and was in no case different from the previously adjusted pH.

17.2 grams of prenol were added to this mixture. The resulting reaction mixture was stirred for a further 4 hours. After this time, samples were taken, cooled immediately in an icebath and then extracted six times with diethyl ether. The combined organic extracts were analyzed by gas chromatography. The yield and selectivity calculations, in each case based on DMVC obtained, are derived from the percentage areas of the GC peaks for the individual compounds.

The results are compiled in Table I below:

TABLE I

| Ex. | Acid | pH | Concentration [Mol/l] | Yield [%] | Selectivity [%] |
|---|---|---|---|---|---|
| C1*) | Phosphoric acid | 1.5 | $160.20 \cdot 10^{-3}$ | 56 | 64 |
| 1 | Phosphoric acid | 2.5 | $40.00 \cdot 10^{-3}$ | 74 | 91 |
| 2 | Phosphoric acid | 3.5 | $0.33 \cdot 10^{-3}$ | 67 | 99 |
| 3 | Adipic acid | 3.1 | $38.32 \cdot 10^{-3}$ | 73 | 96 |
| 4 | Adipic acid | 3.5 | $2.05 \cdot 10^{-3}$ | 48 | 99 |
| 5 | Adipic acid | 4.3 | $0.55 \cdot 10^{-3}$ | 15 | 97 |
| 6 | Citric acid | 3.5 | $0.83 \cdot 10^{-3}$ | 73 | 98 |
| 7 | Hydrochloric acid | 3.3 | $0.50 \cdot 10^{-3}$ | 73 | 96 |

*)Comparative Example. The experiment was terminated after only 3 hours.

Examples 1 to 7 show that the yield and conversion depend on the pH and are virtually independent of the nature of the acid employed, and that the optimal pH range is from 2 to 5.

Comparative Example C1 shows that both the yield and, especially, the selectivity are unsatisfactorily low at a low pH.

Examples 8 to 10

Effect of Temperature

The amount of phosphoric acid necessary to adjust to a pH of 3.5 was dissolved in 500 ml of water. This mixture was introduced with stirring into a reaction vessel and heated to the required temperature.

17.2 grams of prenol were added to this mixture. The acid concentration was $0.33 \times 10^{-3}$ mol per liter of reaction mixture in all cases. The resulting reaction mixture was stirred for a further 4 hours. After this time, samples were taken, immediately cooled in an icebath and then extracted six times with diethyl ether. The combined organic extracts were analyzed by gas chromatography. The yield and selectivity calculations, in each case based on DMVC obtained, are derived from the percentage areas for the GC peaks for the individual compounds.

The results are compiled in Table II below. Example 2 is included to allow better comparison.

TABLE II

| Ex. | Temperature [° C.] | pH | Yield [%] | Selectivity [%] |
|---|---|---|---|---|
| 2 | 80 | 3.5 | 67 | 99 |
| 8 | 70 | 3.5 | 36 | 99 |
| 9 | 60 | 3.5 | 16 | 99 |
| 10 | 50 | 3.5 | 5.8 | 99 |

Examples 2 and 8 to 10 show that the reaction is advantageously carried out above 50° C. to achieve a satisfactory prenol conversion within 4 hours.

Examples 11 and 12

Effect of the Starting Material Concentration

The amount of phosphoric acid needed to adjust to a pH of 2.5 was dissolved in 500 ml of water. This mixture was introduced with stirring into a reaction vessel and heated to 80° C.

Prenol was added to this mixture in an amount of 34.4 grams in one experiment (Example 17) and of 86 grams in another experiment (Example 18). The acid concentration was $40.00 \times 10^{-3}$ mol per liter of reaction mixture in all cases. The mixture of Example 12 comprised two phases. The resulting reaction mixtures were stirred for a further 4 hours. After this time, samples were taken, immediately cooled in an icebath and then extracted six times with diethyl ether. The combined organic extracts were analyzed by gas chromatography. The yield and selectivity calculations, in each case based on DMVC obtained, are derived from the percentage areas of the GC peaks for the individual compounds.

The results are compared with the results for Example I in Table III below.

TABLE III

| Ex. | Amount of prenol [g] | pH | Yield [%] | Selectivity [%] |
|---|---|---|---|---|
| 1 | 17.2 | 2.5 | 74 | 91 |
| 11 | 34.4 | 2.5 | 72 | 84 |
| 12 | 86 | 2.5 | 59 | 74 |

Examples 17 and 18 show, by comparison with Example 1, that increased concentrations of the starting material and, in particular, starting material concentrations resulting in a two-phase reaction mixture distinctly reduce the yield and selectivity of the isomerization.

We claim:

1. A process for isomerizing a precursor allyl alcohol of formula I to a product allyl alcohol of formula II

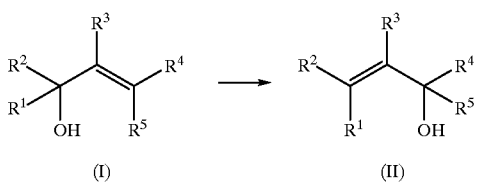

where $R^1$, $-R^2$, $R^3$, $R^4$ and $R^5$ are each independently, H, a linear saturated $C_{1-18}$ alkyl radical, a branched saturated $C_{1-18}$ alkyl radical, a saturated cyclic $C_{3-12}$ alkyl radical, an aromatic radical, an unsaturated radical having one or more double bonds, or an unsaturated radical having one or more triple bonds, in aqueous solution in the presence of protonic acids, wherein a pH of said reaction mixture is adjusted to a range form 2 to 5 either with a protonic acid in a concentration below 0.16 mol per liter of the reaction mixture or with a buffer which comprises a protonic acid.

2. A process as claimed in claim 1, wherein primary or secondary precursor allyl alcohols are isomerized to tertiary product allyl alcohols.

3. A process as claimed in claim 1, wherein the reaction temperature is at least 50° C.

4. A process as claimed in claim 1, wherein the precursor allyl alcohol was present in a concentration of up to 30% by weight in the reaction mixture.

5. A process as claimed in claim 1, wherein 3-methyl-2-buten-1-ol is used as precursor allyl alcohol, and 2-methyl-3-buten-2-ol is prepared as product allyl alcohol.

6. A process as claimed in claim 1, wherein phosphoric acid is used as acid.

7. A process as claimed in claim 1, wherein a citrate buffer is used as buffer.

8. The process of claim 1, wherein $R^1$, $R^2$, $R^3$, $R^4$ and $R^5$ are each independently substituted with a substituent selected from the group consisting of halogen, alkyl and alkoxy.

9. The process of claim 1, wherein said protonic acid is selected from the group consisting of hydrofluoric acid, hydrochloric acid, perchloric acid, hydrobromic acid, sulfuric acid, a sulfonic acid, potassium bisulfate, sodium bisulfate, nitric acid, phosphoric acid, sodium dihydrogen phosphate, potassium dihydrogen phosphate, formic acid, acetic acid, propionic acid, butyric acid, 2-ethylhexanoic acid, benzoic acid, oxalic acid, tartaric acid, succinic acid, maleic acid, furaric acid, adipic acid, citric acid and a mixture thereof.

* * * * *